(12) United States Patent
Bartels et al.

(10) Patent No.: US 7,137,955 B2
(45) Date of Patent: Nov. 21, 2006

(54) METHODS AND SYSTEMS FOR DISTAL RECORDING OF PHONOCARDIOGRAPHIC SIGNALS

(75) Inventors: Keith A. Bartels, San Antonio, TX (US); Kevin S. Honeyager, San Antonio, TX (US); Larry D. Canady, Jr., Bergheim, TX (US)

(73) Assignee: Omron Healthcare Co., Ltd., Kyoto (JP)

( * ) Notice: Subject to any disclaimer, the term of this patent is extended or adjusted under 35 U.S.C. 154(b) by 642 days.

(21) Appl. No.: 10/418,207

(22) Filed: Apr. 18, 2003

(65) Prior Publication Data

US 2003/0220577 A1 Nov. 27, 2003

Related U.S. Application Data

(60) Provisional application No. 60/373,616, filed on Apr. 19, 2002.

(51) Int. Cl.
*A61B 5/04* (2006.01)
(52) U.S. Cl. ..................... 600/528; 600/513
(58) Field of Classification Search ........ 600/485–499, 600/513, 528, 586
See application file for complete search history.

(56) References Cited

U.S. PATENT DOCUMENTS

| | | | |
|---|---|---|---|
| 5,673,692 | A | 10/1997 | Schulze et al. |
| 5,917,918 | A | 6/1999 | Callahan |
| 6,498,854 | B1 | 12/2002 | Smith |
| 2001/0030077 | A1 | 10/2001 | Watson |
| 2002/0016554 | A1 | 2/2002 | Iseberg |
| 2002/0107450 | A1 | 8/2002 | Ogura |
| 2002/0143242 | A1 | 10/2002 | Nemirovski |
| 2003/0163051 | A1* | 8/2003 | Eckerle et al. ............ 600/485 |

FOREIGN PATENT DOCUMENTS

| | | |
|---|---|---|
| EP | 1 050 267 A1 | 11/2000 |
| EP | 1 095 611 A1 | 5/2001 |
| WO | WO 96/23442 | 8/1996 |

OTHER PUBLICATIONS

U.S. Appl. No. 10/418,065, filed Apr. 18, 2003, Honeyager et al.

* cited by examiner

*Primary Examiner*—Jeffrey R. Jastrzab
(74) *Attorney, Agent, or Firm*—Oliff & Berridge, PLC

(57) ABSTRACT

Methods and systems for determining cardiovascular parameters of a patient. In an exemplary embodiment, the method includes placing a phonocardiogram sensor on a patient's body at a first distal location to the heart, and a blood-pressure waveform sensor at a second distal location to the heart. Then, a first set and a second set of waveforms is obtained from the phonocardiogram sensor and the blood-pressure waveform sensor, respectively. A signal processing or conditioning operation may optionally be performed using the first and second sets of waveforms. Then, a time delay between a dicrotic notch signal and an S2 signal is determined. A blood pressure pulse transit time value is calculated by adding S2D, representing a time delay between a patient's heart valve closure time and an arrival time of the S2 signal at the first distal location, to the time delay between a dicrotic notch signal and an S2 signal. Cardiovascular parameters are then determined using the determined blood pressure pulse transit time and at least one physical parameter representative of a arterial distance between a location of the aortic valve and a location of the blood-pressure waveform sensor.

18 Claims, 9 Drawing Sheets

METHODS AND SYSTEMS FOR DISTAL RECORDING OF PHONOCARDIOGRAPHIC SIGNALS

BACKGROUND OF THE INVENTION

1. Field of Invention

This invention relates to systems and methods for recording of phonocardiogram (PCG) signals at locations distal to the heart.

2. Description of Related Art

Sound signals recorded from the heart are called phonocardiogram (PCG) signals. A healthy heart generates two distinct sounds that are coincident with the closure of the heart valves. These two sounds are called the first heart sound (S1) and the second heart sound (S2). In particular, S2 is coincident with the closure of the aortic valve. The closure of the aortic valve also creates a distinct feature on the arterial blood pressure waveform called the dicrotic notch. The pulse transit time (PTT) is defined as the time required for an arterial blood pressure pulse to travel from the heart to a distal location to the heart. The PTT can be measured by determining the delay between the closure of the aortic valve and the arrival of the dicrotic notch at a distal measurement point. This measurement is possible since, by placing a phonocardiogram (PCG) sensor on the chest near the aortic valve, it can be assumed that the delay between the closure of the valve and the measurement of the S2 sound on the chest is negligible. The arterial blood pressure pulse wave velocity (PWV) is computed by dividing the arterial path length between the heart and the measurement point by the PTT. Because the PWV is dependent on the stiffness of the arterial walls, it can be a useful parameter in determining the health of the cardiovascular system (e.g. arteriosclerosis).

Conventional methods and devices measure PWV using a PCG sensor in a standard location on the chest and a blood pressure waveform measurement at points distal to the heart. When PTT/PWV is to be measured using a PCG sensor at a location distal to the heart, the true PTT/PWV cannot be calculated unless one accounts for the propagation delay, hereinafter referred to as S2D, where S2D is the measured delay between the valve closure and the arrival of second heart sound (S2) at the distal location. The accuracy of the PTT/PWV measurement is directly proportional to the accuracy with which S2D is known.

SUMMARY OF THE INVENTION

One method or technique that can be used to measure a patient's physiological parameters includes determining an S2D value for each individual patient using a calibration step. That S2D value is then added to the subsequent delay time (DT) measurements to determine the PTT.

Another method or technique that can be used to measure a patient's physiological parameters includes determining an S2D value from knowledge of the general population. This S2D value may be adjusted for the individual's height or other physical parameters. The S2D value is then added to the subsequent DT measurements to determine the PTT.

Yet another method or technique that can be used to measure a patient's physiological parameters does not require determining an S2D value. The delay time alone (DT) and derived measurements, such as, for example, a Pulse Wave Velocity Index (PWVI) are used to provide critical trending information for a given patient. The delay time DT and Pulse Wave Velocity Index, PWVI, are not actual propagation parameters, but are highly dependent on them.

This invention provides systems and methods for obtaining phonocardiogram signals at a location distal to the heart.

This invention separately provides systems and methods for obtaining timing of heart valve closure.

This invention separately provides systems and methods for enhancing distal phonocardiogram recording.

This invention separately provides systems and methods for determining corrected blood-pressure pulse transit time (PTT).

This invention separately provides systems and methods for determining arterial blood pressure pulse wave velocity (PWV).

This invention separately provides systems and methods for determining arterial blood pressure pulse wave velocity index (PWVI).

This invention separately provides systems and methods for determining the heart's pre-ejection period (PEP) or isovolumetric contraction period.

This invention separately provides systems and methods for determining S2D, the delay between a patient's heart valve closure and the arrival of the patient's S2 heart sound at a distal location.

This invention separately provides systems and methods for determining DT, the delay time between a dicrotic notch signal and an S2 signal.

In various exemplary embodiments of the systems and methods according to this invention, PCG signals are obtained by placing a vibration sensor, a pressure sensor, a displacement sensor or the like on a bone located distal to the heart.

In various exemplary embodiments of the systems and methods according to this invention, PCG signals are obtained by placing a vibration sensor, a pressure sensor, a displacement sensor or the like on tissue located distal to the heart.

In various exemplary embodiments of the systems and methods according to this invention, timing of heart valve closure is obtained by using heart sound (phonocardiogram, PCG) signals measured on bone or tissue distal to the heart.

In various exemplary embodiments of the systems and methods according to this invention, an enhanced distal phonocardiogram (PCG) recording is performed using a signal conditioning or processing operation of the signals triggered by the R-wave of the electrocardiogram (ECG).

In various exemplary embodiments of the systems and methods according to this invention, an enhanced distal phonocardiogram (PCG) recording using a signal conditioning or processing operation is performed using ensemble averaging triggered by the R-wave of the ECG.

In various exemplary embodiments of the systems and methods according to this invention, an enhanced distal phonocardiogram (PCG) recording is performed using a signal conditioning or processing operation of the phonocardiogram signals triggered by the dicrotic notch of the blood-pressure waveform.

In various exemplary embodiments of the systems and methods according to this invention, the S2 of a PCG sensor other than the distal sensor is used as a trigger signal.

In various exemplary embodiments of the systems and methods according to this invention, an enhanced distal PCG recording using a signal conditioning or processing operation is performed using an ensemble averaging operation of the PCG signals triggered by the dicrotic notch of the blood-pressure waveform.

In various exemplary embodiments of the systems and methods according to this invention, DT, the delay time between a dicrotic notch signal and an S2 signal, is determined by using a recording of the blood pressure waveform and a recording of the PCG signal, both acquired from a location distal to the heart.

In various exemplary embodiments of the systems and methods according to this invention, a corrected PTT is determined by adding S2D to DT.

In various exemplary embodiments of the systems and methods according to this invention, PWV is determined using the corrected PTT and artery length.

In various exemplary embodiments of the systems and methods according to this invention, PEP is determined using the distally obtained valve-closure time in combination with the ECG signal and the blood pressure waveform.

In various exemplary embodiments of the systems and methods according to this invention, PWVI is determined using DT.

In various exemplary embodiments of the systems and methods according to this invention, determining cardiovascular parameters, such as, for example, PTT, PWV, PWVI and PEP, is performed using a device having a plurality of sensors placed in close proximity to each other at a location distal to the heart.

In various exemplary embodiments of the systems and methods according to this invention, measuring S2D, DT and the like is performed using a device having a plurality of sensors placed in close proximity to each other at a location distal to the heart.

In various exemplary embodiments of the systems and methods according to this invention, measuring S2D, DT and the like is performed using a device having a plurality of sensors placed in close proximity to each other at a location distal to the heart, in combination with a PCG sensor positioned on a patient's chest near the patient's heart.

BRIEF DESCRIPTION OF THE DRAWINGS

Various exemplary embodiments of this invention will be described in detail, with reference to the following figures, wherein.

DETAILED DESCRIPTION OF EXEMPLARY EMBODIMENTS

As described herein, this invention provides systems and methods for acquiring useful PCG information at locations far or distal to the heart.

Heart sounds are conducted to distal locations at a rate faster than the blood pressure PWV. Propagation to distal locations is fastest along a bone path. Propagation through generalized body tissues is somewhat slower than in bone, but still faster than the PWV. Therefore, this invention can be implemented using PCG signals that travel to the distal location via bone, generalized tissue paths, or the like.

Figure 1:
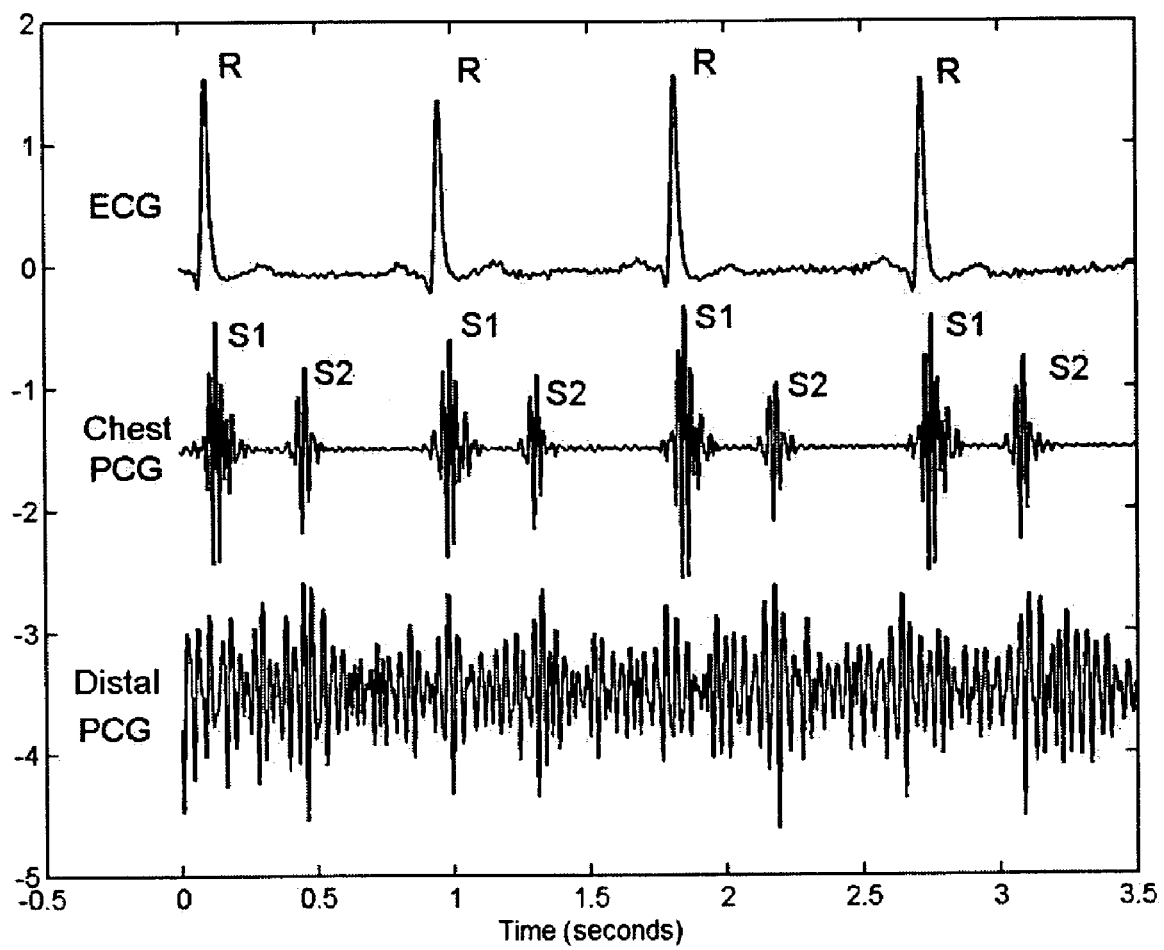
FIG. 1 is a graph plotting a typical person's ECG, PCG measured on the chest and PCG measured at a distal location to the heart, for example, at the olecranon (bone at the elbow)

FIG. 1 shows a plot of a typical person's ECG, PCG measured on the chest and PCG measured at a distal location to the heart, for example at the olecranon (bone at the elbow). As shown in FIG. 1, the S1 and S2 signals can be difficult to identify in the data taken from the distal location, e.g., elbow. The PCG data shown in FIG. 1 were acquired using a commercially available PCG sensor that uses a condenser microphone technology. Similar results are obtained using other technologies such as piezoelectric materials and accelerometers. The waveform data shown were enhanced by a digital bandpass filter that passed frequencies between 25 and 55 Hz.

This invention provides systems and methods that improve the signal-to-noise ratio (SNR) of the acquired or measured heart sounds by improving signal processing. In various exemplary embodiments, improving signal conditioning or processing, and thus improving signal-to-noise ratio (SNR) of the acquired or measured heart sounds, is performed by averaging two or more consecutive heart cycles, also called an ensemble averaging.

Figure 2:
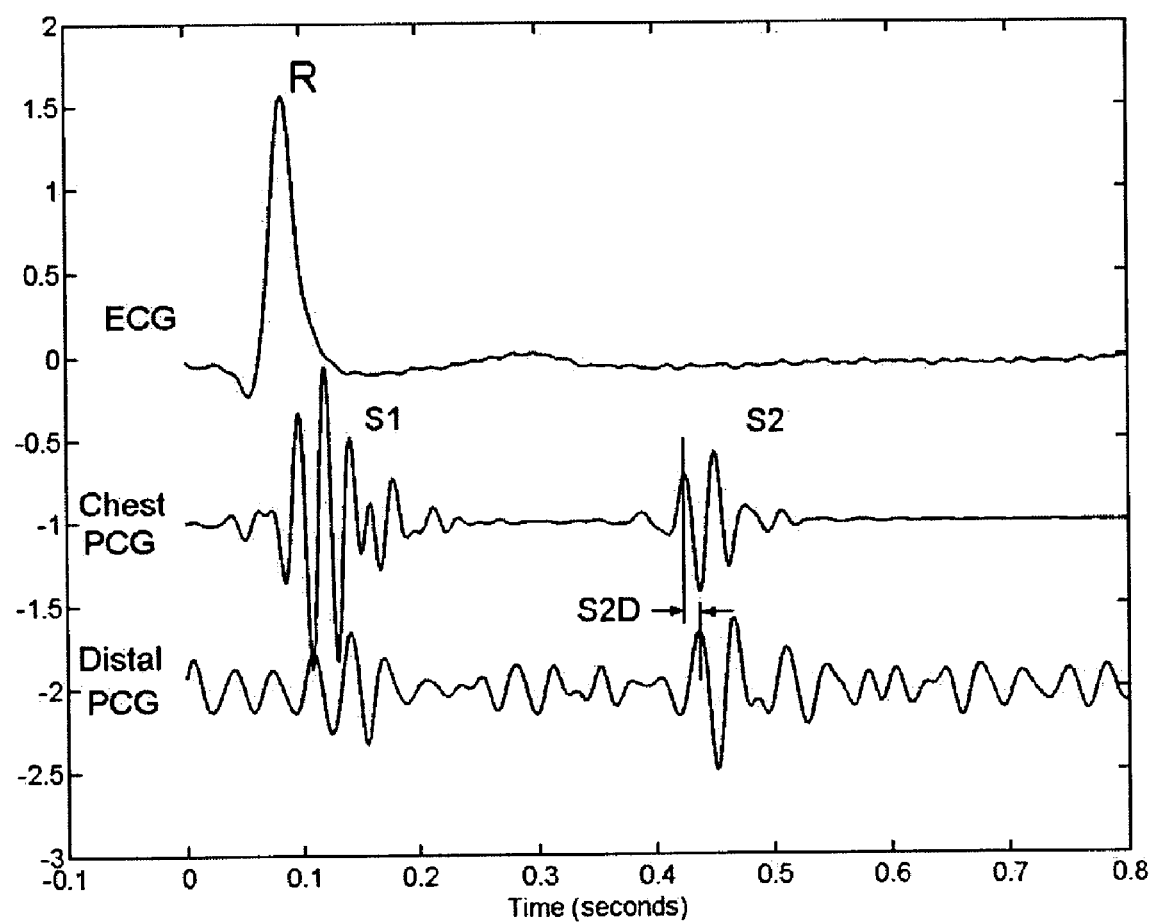
FIG. 2 is a graph plotting the result of beat-to-beat ensemble averaging using R-wave triggering of the data shown in FIG. 1.

To perform the ensemble averaging, the individual heart cycles must first be identified. This can be done by detecting a unique feature from each heart cycle. In one exemplary embodiment, the R-wave of the ECG signal is used as the delimiter of heart cycles. This is called R-wave triggering of the ensemble averaging. FIG. 2 shows the result of R-wave triggering of the data in FIG. 1. Approximately 10 seconds of data were used to obtain this average heart cycle information. As shown in FIG. 2, the noise is greatly reduced in the distal or elbow PCG data. Furthermore, as shown in FIG. 2, a time delay (labeled S2D) exists between the chest S2 signal and distal or elbow S2 signal of the PCG waveform.

Figure 3:
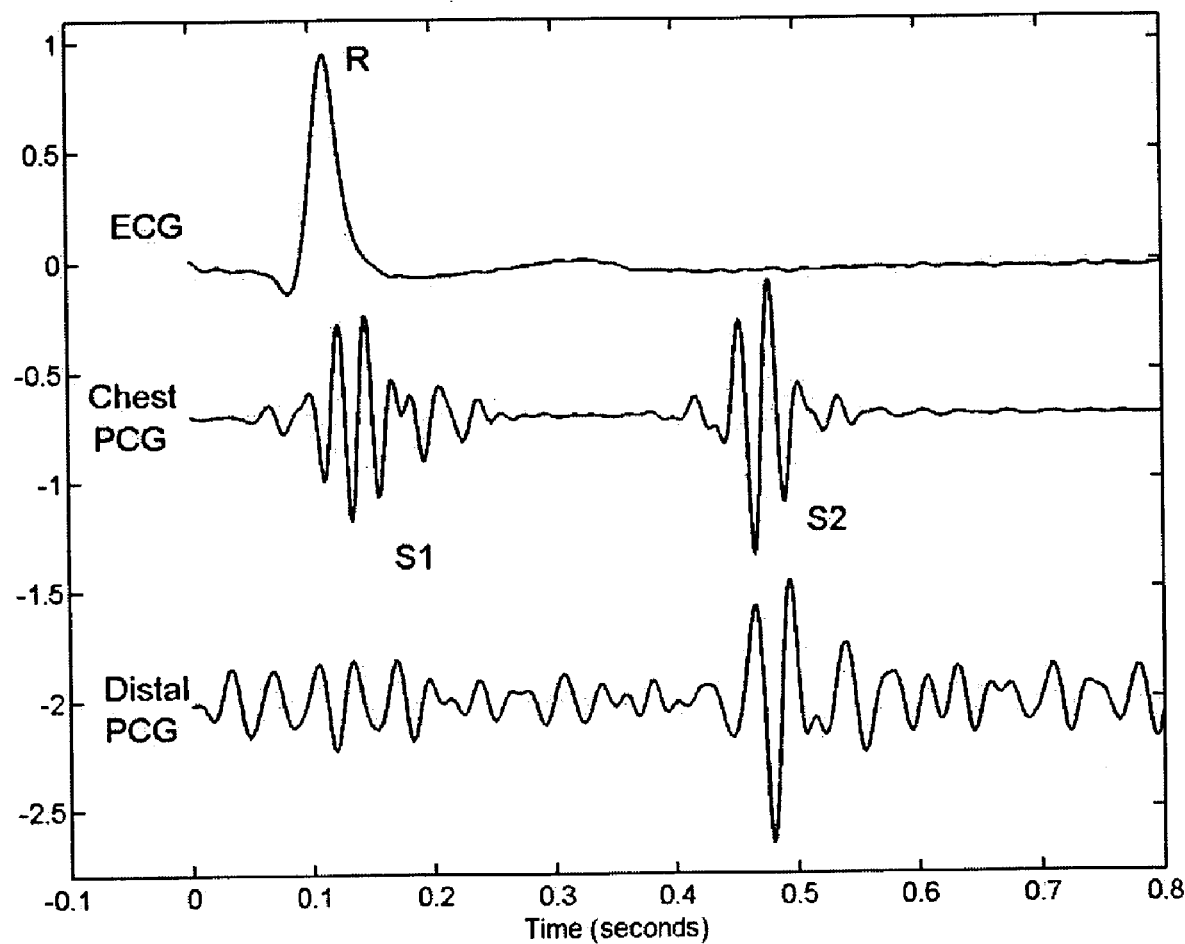
FIG. 3 is a graph plotting the result of beat-to-beat ensemble averaging using S2 triggering of the data shown in FIG. 1.

In another exemplary embodiment, the S2 signal of the chest PCG sensor can be used to delimit the heart cycles. FIG. 3 shows the result of using the S2 signal from the chest PCG to trigger the ensemble averaging. Approximately 10 seconds of data were used to obtain this average heart cycle information. Using the S2 trigger is advantageous over the R-wave trigger in that a higher signal-to-noise ratio (SNR) for the averaged S2 signal is obtained. This is because there is a variability from heart cycle to heart cycle of the time between the R-wave and the S2 signal. This variability causes a "jitter" of the S2 signal when using the R-wave trigger and hence some signal amplitude can be averaged away.

Figure 4:
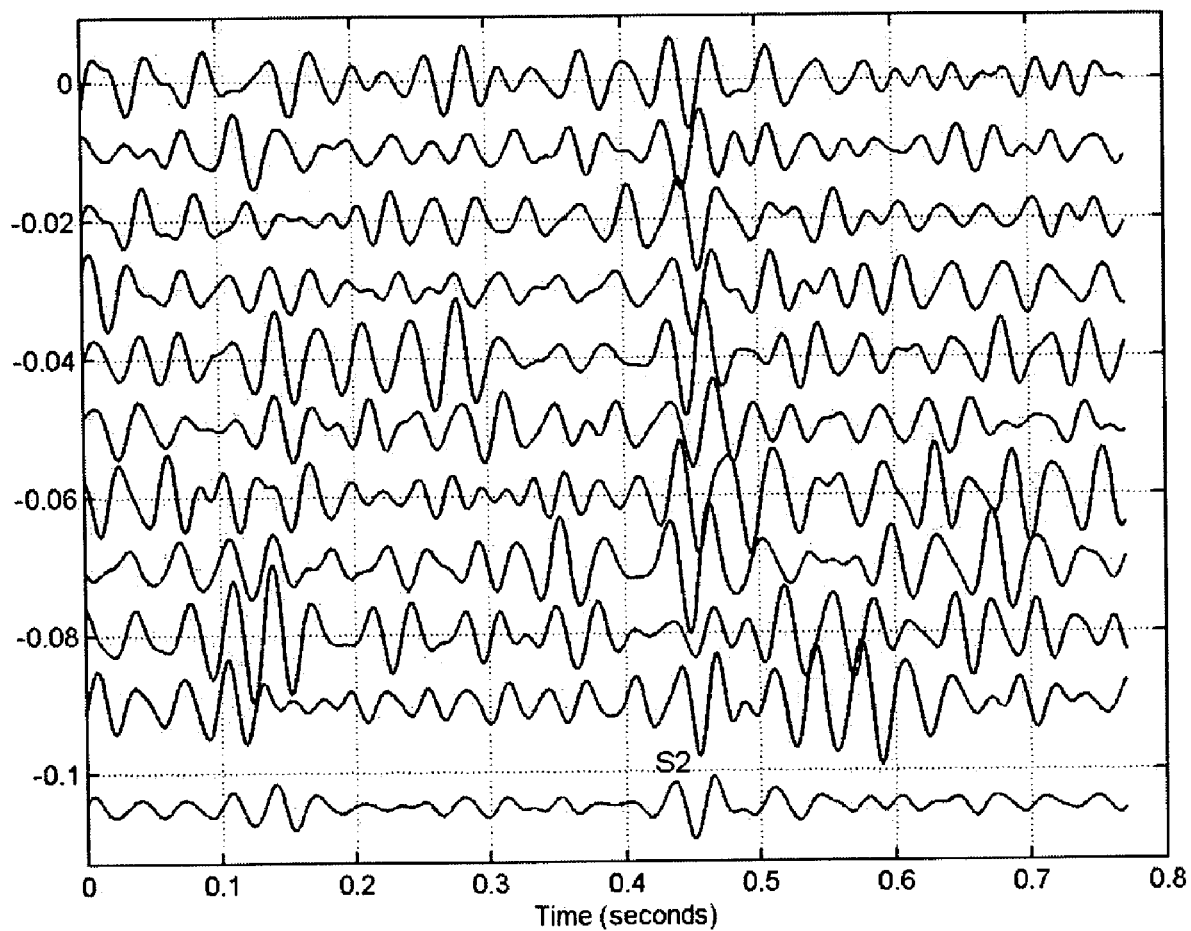
FIG. 4 is a graph plotting the result of beat-to-beat ensemble averaging of ten signal measurements using R-wave triggering.

The R-wave trigger is advantageous in that it is easily performed. The R-wave of the ECG is a very easily identifiable signal. The utility of ensemble averaging is shown in FIG. 4. This ensemble averaging was performed with R-wave triggering and the signal was filtered with a 25–55 Hz bandpass filter prior to averaging. The signal at the bottom of the graph is the ensemble averaged signal of the ten signals illustrated above the bottom signal in FIG. 4. As shown in FIG. 4, the SNR of the averaged signal at the bottom of the graph is much improved than of any of the individual unaveraged signals.

The advantage of the S2-triggered ensemble averaging could also be obtained by using the dicrotic notch of the blood pressure waveform as the trigger. The dicrotic notch and S2 signal both result from the closure of the aortic valve and hence have the same timing.

Figure 5:
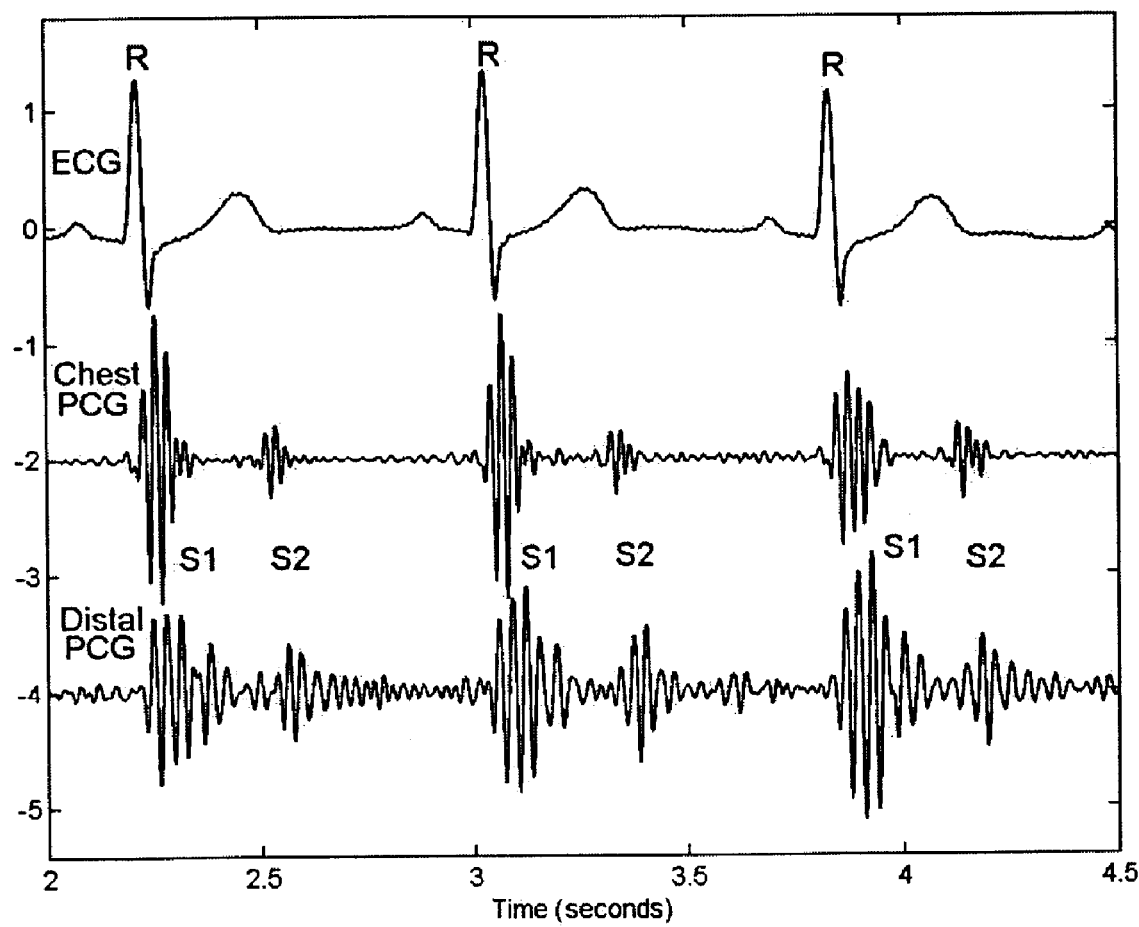
FIG. 5 is a graph plotting the result of ECG, chest PCG and distal PCG signal measurements without ensemble averaging.

It will be noted that in various exemplary embodiments of the systems and methods according to this invention, ensemble averaging is not required to be performed to detect the S2 signal at a distal location to the heart. For example, FIG. 5 illustrates a typical person's ECG, PCG measured on the chest and PCG measured at a distal location to the heart, for example at the olecranon (bone at the elbow). As shown in FIG. 5, the S2 signal can be easily identified or determined in the data taken from the distal location, e.g., elbow, without having to perform a signal conditioning or processing operation such as an ensemble averaging operation. The SNR of the distal S2 signal is high due to relatively low noise from sources (other than the heart valves) within the body and from building vibrations. That is, ensemble averaging may not be required if building noise and/or body vibration is low or negligible.

As described above, the PTT is measured with current technology as the time between the S2 signal measured on the chest and the dicrotic notch of the arterial blood pressure waveform. In various exemplary embodiments of the systems and methods according to this invention, the PTT is measured as the time between the distally measured S2 signal and the dicrotic notch plus S2D, where S2D is the measured delay between the valve closure and the arrival of the S2 signal at the distal location.

In one exemplary embodiment, the S2D value could be determined as an average value for the entire population (possibly adjusted for the person's artery length). In another exemplary embodiment, a predetermined S2D value for the particular individual may be used. In yet another exemplary embodiment, the S2D value could be experimentally determined based on patient demographics.

The predetermined S2D value could be obtained for an individual by using a first PCG sensor, for example a chest PCG sensor, during a calibration step. The S2D would be measured as the time delay between the chest PCG measurement and the distal PCG measurement. An individually calibrated value for S2D adds an additional initial step to using the device, but would give a more accurate measurement than if a population-based standardized value was used. For some applications, however, the standardized S2D value would give sufficiently accurate results.

In various exemplary embodiments of the systems and methods according to this invention, a patient's physiological parameters, such as, for example PWVI, can be obtained by using the delay time (DT) between dicrotic notch and S2 signals without using the S2D signal. That is, an index of PWV, e.g., PWVI, can be determined without having to determine the S2D signal. The PWVI monitored over time would still show increases or decreases in PWV.

Figure 6:
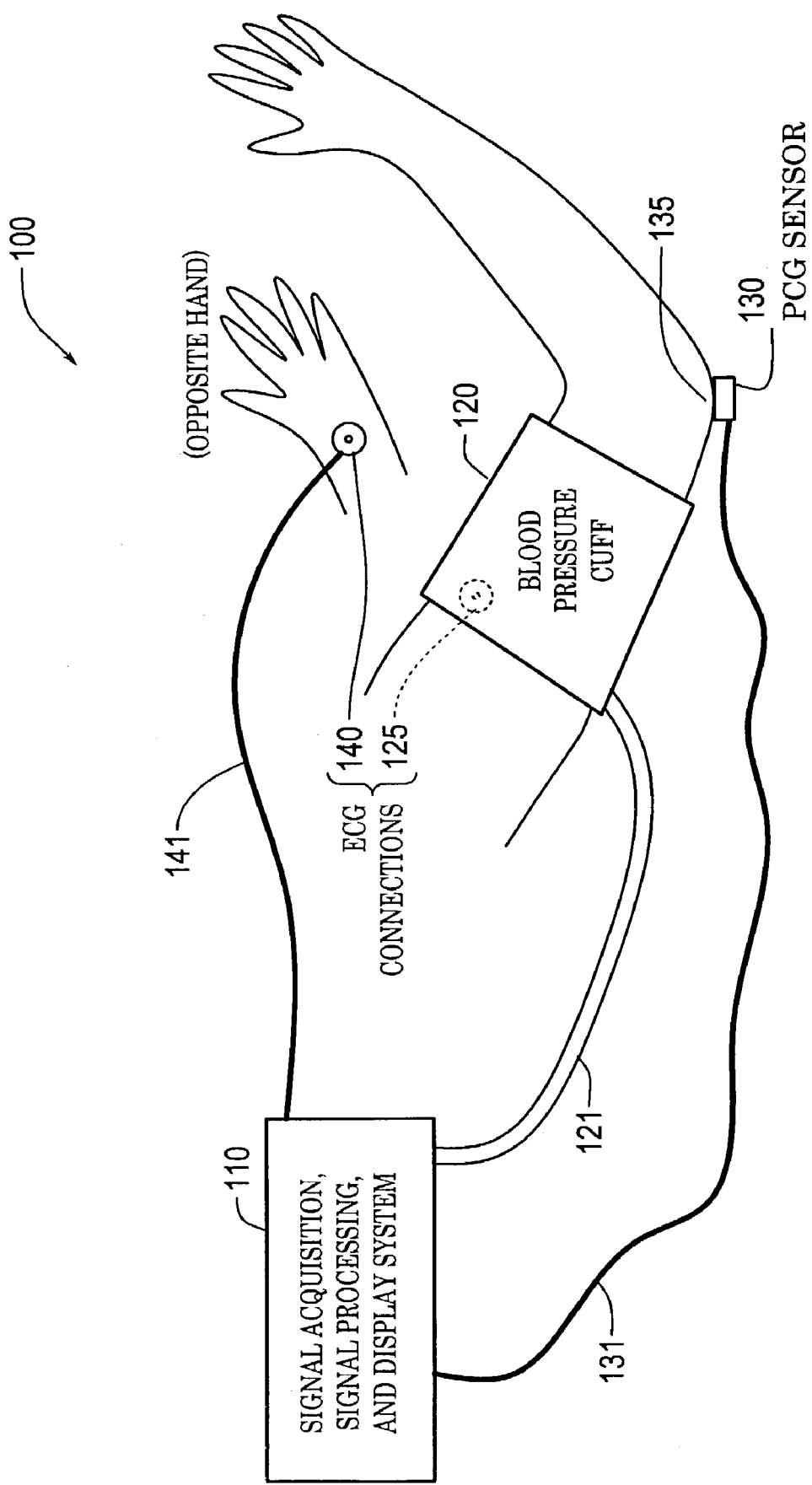
FIG. 6 is a schematic illustration of one exemplary embodiment of a system used to determine cardiovascular parameters, such as, for example, PTT, PWV, PWVI and PEP.

FIG. 6 shows one exemplary embodiment of a system 100 according to this invention in which blood pressure waveforms and PCG readings are performed on the arm. The blood pressure waveform is collected from the blood pressure cuff 120 using known art. That is, the cuff 120 is inflated to a constant pressure and the changing pressure in the cuff 120 is recorded by the signal acquisition/processing/display system 110. The changing pressure in the cuff 120 corresponds to the changing pressure-in the brachial artery in the arm under the cuff. The PCG signal is measured at the olecranon 135 area of the elbow in this example using the PCG sensor 130. Signals are transmitted to the signal acquisition/processing/display system 110 via connection paths 121, 131, 141.

As shown in FIG. 6, ECG electrodes 125 and 140 are used to monitor the heart's electrical signals. This is necessary if R-wave triggering of the ensemble averaging is required. As discussed above, the ECG connections are optional if no ensemble averaging is performed or if the dicrotic notch of the blood pressure waveform is used as the trigger. Signals from the blood pressure waveform recording device 120, PCG sensor 130, and ECG connections 125, 140 are transmitted to the signal acquisition/processing/display system 110 via connection paths 121, 131, 141. ECG electrodes 125 and 140 may be positioned on various locations of a patient's body, including for example, on a patient's arm. Further, the electrodes may be included as part of an arm cuff device or the like.

It will be appreciated by those skilled in the art that the system 100 shown in FIG. 6 represents one exemplary embodiment of the types of devices that may be used with this invention. Furthermore, other exemplary embodiments could be used at other locations on the body, such as other parts of the arm (the wrist), or on the leg.

For example, in one exemplary embodiment, the device used to record blood pressure waveform includes a blood pressure cuff apparatus. In another exemplary embodiments, recording a blood pressure waveform may be performed using a device such as, for example, an arterial tonometer.

Figure 7:
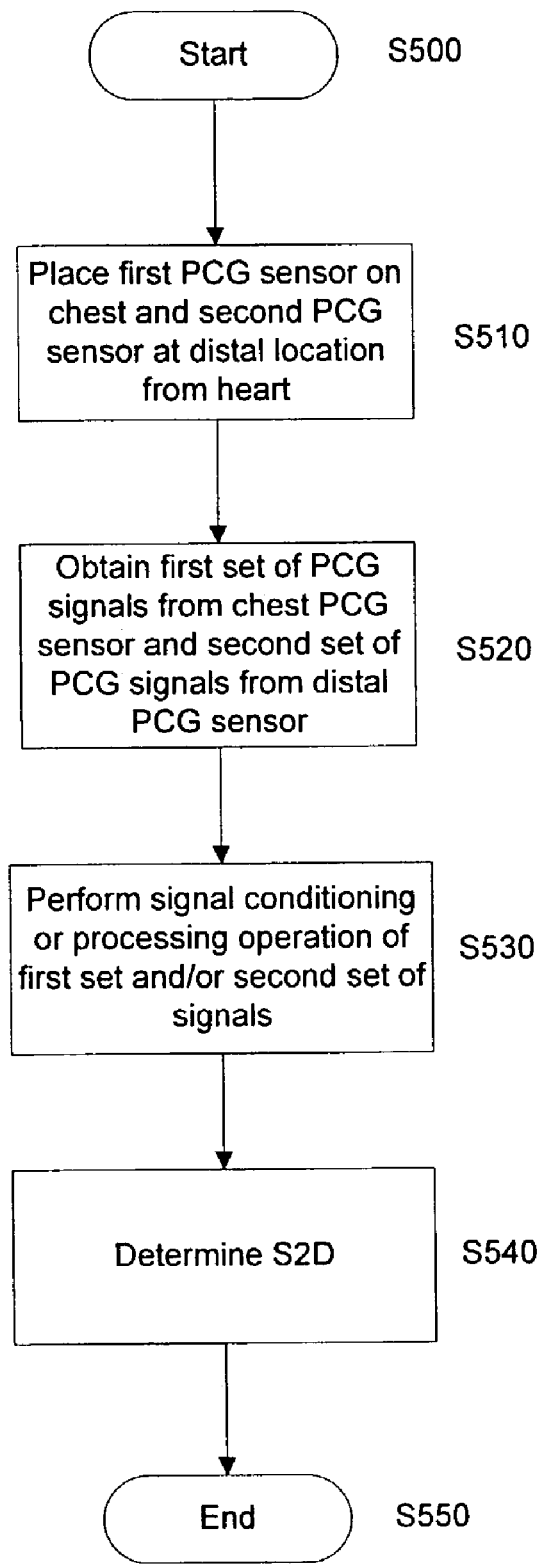
FIG. 7 is a flowchart outlining one exemplary embodiment of a method for determining S2D, the delay between the valve closure and the arrival of a second heart sound (S2) at a distal location, for a patient.

FIG. 7 is a flowchart outlining one exemplary embodiment of a method for determining S2D. The various steps of the method shown in FIG. 6 are generally performed only occasionally for each individual.

As shown in FIG. 7, the method starts at step S500 and continues to step S510 where a first PCG sensor is placed on a patient's chest and a second PCG sensor is placed at a distal location to the heart. Next, at step S520, data are acquired from both sensors, for example, a first set of PCG signals are obtained or acquired using the first PCG sensor and a second set of PCG signals are obtained or acquired using the second PCG sensor. Data may be acquired simultaneously or close in time to each other.

Then, at step S530, a signal processing or conditioning operation is performed using the first and second sets of PCG signals acquired. In an exemplary embodiment of the systems and methods according to this invention, an ensemble averaging operation is performed using the first and second sets of PCG signals acquired. In another exemplary embodiment of the systems and methods according to this invention, signal processing or conditioning 530 may be performed using a bandpass filter. In yet another exemplary embodiment of the systems and methods according to this invention, signal processing is performed for determining a stable detection point in the distal or elbow S2 signal.

Next, at step S540, using the results obtained from the signal processing or conditioning operation, such as for example from an ensemble averaging operation, the S2D is determined. The method then continues to step S550, where the method stops.

Figure 8:
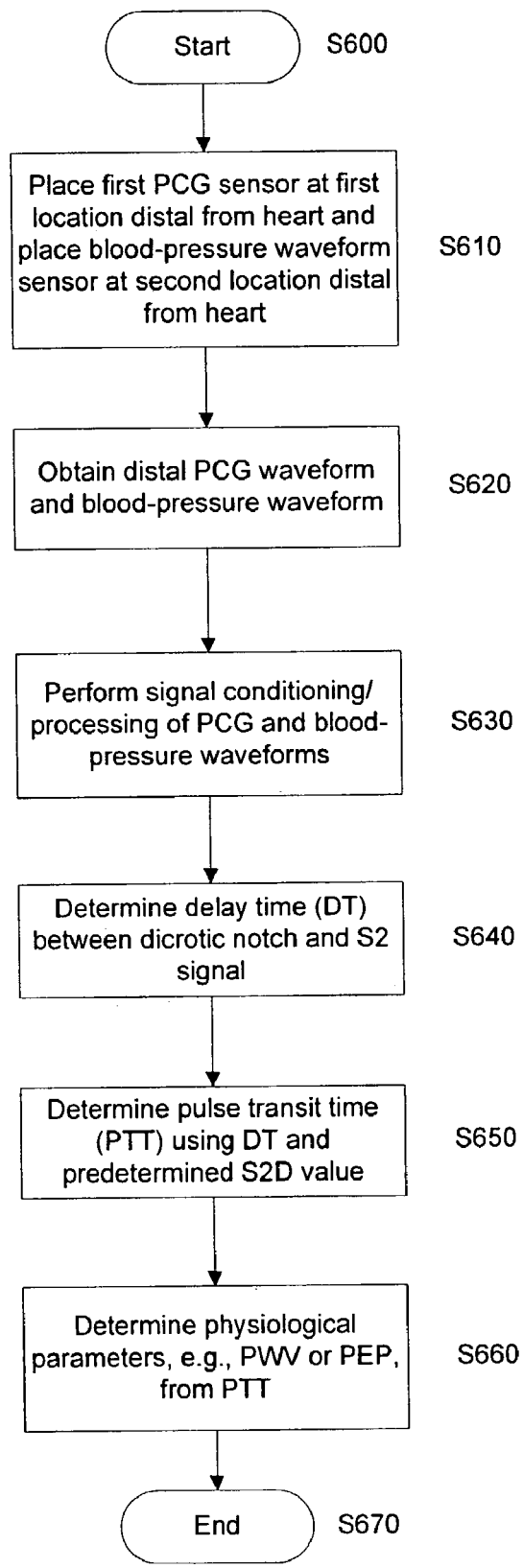
FIG. 8 is a flowchart outlining one exemplary embodiment of a method for determining and/or measuring physiological parameters of a patient, including cardiovascular parameters, such as, for example, PTT, PWV and PEP, using a determined S2D value.

FIG. 8 is a flowchart outlining one exemplary embodiment of a method for determining physiological parameters, including for example, PWV, PEP and the like, by using distally measured heart sounds. In one exemplary embodiment, the timing of the closure of the aortic valve in combination with the ECG and blood pressure waveform can be used to compute the heart's pre-ejection period (PEP). PEP is also known as the isovolumetric contraction period and is the time during which ventricular pressure is increasing while the aortic valve is still closed. When the pressure within the ventricle surpasses the aortic pressure the aortic valve opens and the PEP ends. PEP, especially when used in ratio to the ventricular ejection time, is another important parameter indicating cardiovascular health.

As shown in FIG. 8, the method starts at step S600 and continues to step S610 where a phonocardiogram sensor is placed on a patient's body at a first distal location to the heart, and a blood-pressure waveform sensor is placed at a second distal location to the heart. Next, at step 620, a first set of waveforms is obtained from the phonocardiogram sensor. A second set of waveforms is also obtained from the blood-pressure waveform sensor.

Then, at step S630, a signal conditioning/processing operation, such as for example, an ensemble averaging operation, may optionally be performed using the first and second sets of waveforms obtained in step S620. The operation continues to step S640, where a time delay (DT) between a dicrotic notch signal and an S2 signal is determined.

At step S650, a blood pressure pulse transit time (PTT) value is determined by adding a previously determined or known value of S2D, representing a time delay between a patient's heart valve closure time and an arrival time of the S2 signal at the first distal location, to the time delay DT between a dicrotic notch signal and a distal S2 signal.

Next, at step S660, various cardiovascular parameters of a patient are determined using the determined blood pressure pulse transit time calculated in step S650 and at least one physical parameter representative of an arterial distance between a location of the phonocardiogram sensor and a location of the blood-pressure waveform sensor. The method then continues to step S670 where the method stops.

In one exemplary embodiment, the method shown in FIG. 8 is used to determine arterial blood pressure pulse wave velocity (PWV) by dividing the arterial path length between the heart and the distal measurement point by the PTT. Because the pulse wave velocity is dependent on the stiffness of the arterial walls, PWV can be a useful parameter in determining the health of the cardiovascular system (e.g. arteriosclerosis).

In one exemplary embodiment of the method according to this invention, step S630, performing a signal conditioning/processing operation, for example, an ensemble averaging operation, includes determining a patient's individual heart cycles. In one exemplary embodiment, determining a patient's individual heart cycles includes determining a delimiter in the patient's individual heart cycles. Determining a delimiter of heart cycles may be performed by determining an R-wave using the first set of electrocardiogram signals. Alternatively, determining a delimiter of heart cycles may be performed by determining an S2 signal, representative of a second heart sound associated with closure of the heart valves, from the first set of PCG signals.

In various exemplary embodiments of the systems and methods according to this invention, performing a signal conditioning/processing operation, for example, an ensemble averaging operation, may include using dicrotic notch of arterial blood pressure waveform as a trigger.

In will be appreciated by those skilled in the art that the distal location may include a patient's elbow area or other parts of the body. Furthermore, the PCG sensor(s) may be placed on or around bone or bone structure, or on tissue.

Furthermore, it will be appreciated by those skilled in the art that the blood pressure waveform sensor may include a blood pressure cuff, an arterial tonometer, or other sensor sensitive to the blood pressure waveform.

Figure 9:
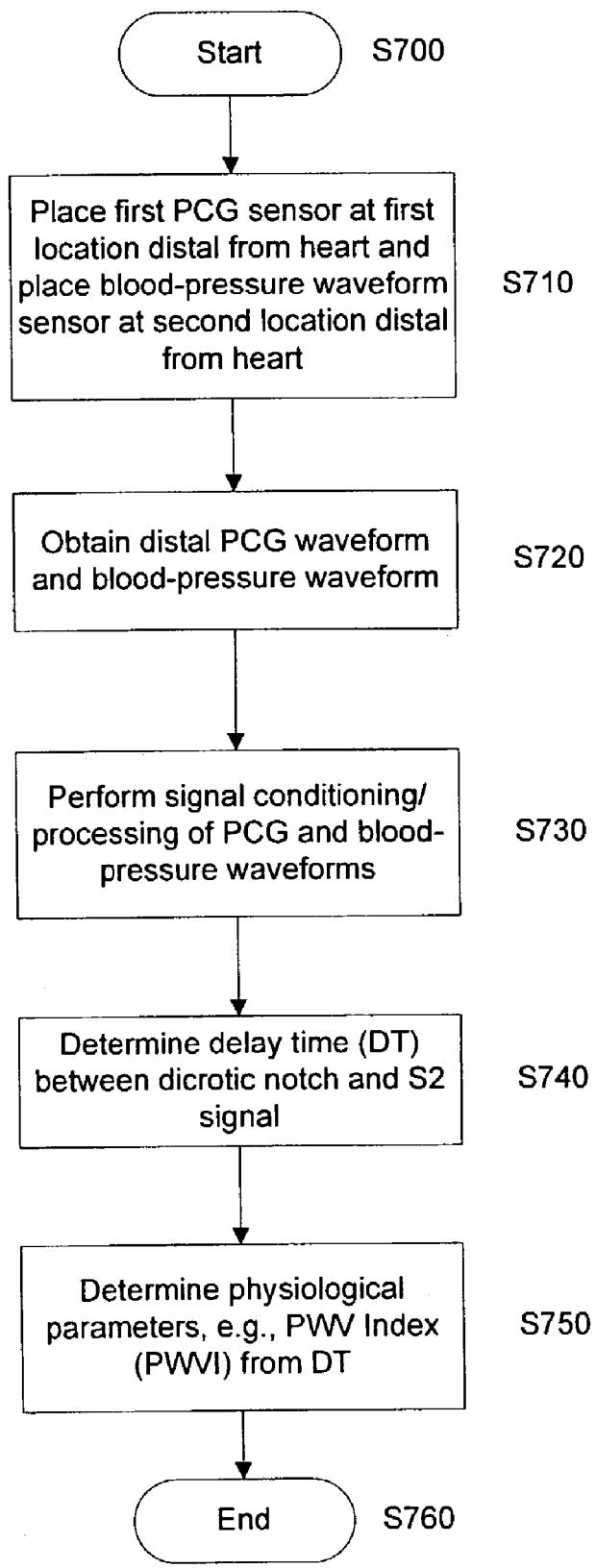
FIG. 9 is a flowchart outlining another exemplary embodiment of a method for determining and/or measuring physiological parameters of a patient, including cardiovascular parameters, such as, for example, PWVI, without using a determined S2D value.

FIG. 9 is a flowchart outlining another exemplary embodiment of a method for determining physiological parameters, including for example, PWVI and the like, by using distally measured heart sounds.

As shown in FIG. 9, the method starts at step S700 and continues to step S710 where a phonocardiogram sensor is placed on a patient's body at a first distal location to the heart, and a blood-pressure waveform sensor is placed at a second distal location to the heart. Next, at step 720, a first set of waveforms is obtained from the phonocardiogram sensor. A second set of waveforms is also obtained from the blood-pressure waveform sensor.

Then, at step S730, a signal conditioning/processing operation, such as for example, an ensemble averaging operation, may optionally be performed using the first and second sets of waveforms obtained in step S720. The operation continues to step S740, where a time delay (DT) between a dicrotic notch signal and an S2 signal is determined.

Next, at step S750, various cardiovascular parameters of a patient are determined using the determined delay time DT calculated in step S740. In one exemplary embodiment, the method shown in FIG. 9 is used to determine arterial blood pressure pulse wave velocity index (PWVI). Because the pulse wave velocity is dependent on the stiffness of the arterial walls, PWVI can be a useful parameter in determining the health of the cardiovascular system (e.g. arteriosclerosis). The method then continues to step S760 where the method stops.

In one exemplary embodiment of the method according to this invention, step S730, performing a signal conditioning/processing operation, for example, an ensemble averaging operation, includes determining a patient's individual heart cycles. In one exemplary embodiment, determining a patient's individual heart cycles includes determining a delimiter in the patient's individual heart cycles. Determining a delimiter of heart cycles may be performed by determining an R-wave using the first set of electrocardiogram signals. Alternatively, determining a delimiter of heart cycles may be performed by determining an S2 signal, representative of a second heart sound associated with closure of the heart valves, from the first set of electrocardiogram signals.

In various exemplary embodiments of the systems and methods according to this invention, performing a signal conditioning/processing operation, for example, an ensemble averaging operation, may include using dicrotic notch of arterial blood pressure waveform as a trigger.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention as defined in the following claims.

What is claimed is:

1. A method to determine a S2D value representing a time delay between a patient's heart valve closure and an arrival of a patient's S2 heart sound at a distal location to the heart, the method comprising:
   placing a first phonocardiogram sensor on a patient's chest;
   placing a second phonocardiogram sensor at the distal location to the heart;
   obtaining a first set of phonocardiogram signals from the first phonocardiogram sensor;
   obtaining a second set of phonocardiogram signals from the second phonocardiogram sensor;
   performing a signal processing or conditioning operation using the first and second sets of phonocardiogram signals; and
   determining the time delay based on results obtained from the signal processing or conditioning operation.

2. The method according to claim 1, wherein performing a signal processing or conditioning operation comprises determining a patient's individual heart cycles.

3. The method according to claim 2, wherein determining a patient's individual heart cycles comprises determining a delimiter in the patient's individual heart cycles.

4. The method according to claim 3, wherein determining a delimiter of heart cycles comprises determining an R-wave using a first set of electrocardiogram signals obtained from at least one electrocardiogram sensor positioned on the patient's body.

5. The method according to claim 3, wherein determining a delimiter of heart cycles comprises determining an S2 signal, representative of a second heart sound associated with closure of the heart valves, from the first set of phonocardiogram signals.

6. The method according to claim 5, wherein performing a signal processing or conditioning operation includes using dicrotic notch of arterial blood pressure waveform as a trigger.

7. The method according to claim 1, wherein the distal location is a patient's elbow.

8. The method according to claim 1, wherein placing the second phonocardiogram sensor at the distal location comprises placing the second phonocardiogram sensor on a bone or a tissue at the distal location.

9. The method according to claim 1, wherein performing a signal processing or conditioning operation comprises one or more of performing an ensemble averaging operation, using a bandpass filter, and determining a stable detection point on a distal S2 signal.

10. A method for determining cardiovascular parameters of a patient, the method comprising:
    placing a phonocardiogram sensor on a patient's body at a first distal location to the heart;
    placing a blood-pressure waveform sensor at a second distal location to the heart;
    obtaining a first set of waveforms from the phonocardiogram sensor;
    obtaining a second set of waveforms from the blood-pressure waveform sensor;
    performing a signal processing or conditioning operation using the first and second sets of waveforms;
    determining a time delay between a dicrotic notch signal detected from the second set of waveforms and an S2 signal detected from the first set of waveforms;
    determining a blood pressure pulse transit time value by adding S2D, representing a time delay between a patient's heart valve closure time and an arrival time of the S2 signal at the first distal location, to the time delay between a dicrotic notch signal and the S2 signal; and
    determining cardiovascular parameters of a patient using the determined blood pressure pulse transit time and at least one physical parameter representative of a arterial distance between a location of aortic valve of the heart and a location of the blood-pressure waveform sensor.

11. The method according to claim 10, wherein cardiovascular parameters include blood pressure-wave velocity, a patient's heart isovolumetric contraction period or the like.

12. The method according to claim 10, wherein performing a signal processing or conditioning operation comprises one or more of performing an ensemble averaging operation, performing a processing using a bandpass filter, and performing a processing to determine a stable detection point on a distal S2 signal.

13. A method for determining a corrected blood pressure pulse transit time value for a patient, the method comprising:
    placing a phonocardiogram sensor on a patient's body at a first distal location to the heart;
    placing a blood-pressure waveform sensor at a distal location on the patient's body;
    obtaining a first set of waveforms from the phonocardiogram sensor;
    obtaining a second set of waveforms from the blood-pressure waveform sensor;
    performing a signal processing or conditioning operation using the first and second sets of waveforms; and
    determining a time delay between a dicrotic notch signal detected from the second set of waveforms and an S2 signal detected from the first set of waveforms;
    determining a corrected blood pressure pulse transit time value by adding S2D, representing a time delay between a patient's heart valve closure time and an arrival time of the S2 signal at the first distal location, to the time delay between a dicrotic notch signal and an S2 signal.

14. The method according to claim 13 wherein performing a signal processing or conditioning operation comprises one or more of performing an ensemble averaging operation, performing a processing using a bandpass filter, and performing a processing to determine a stable detection point on a distal S2 signal.

15. A system for determining cardiovascular parameters of a patient, the system comprising:
    a signal acquisition and processing device;
    a blood pressure waveform measuring device coupled to the signal acquisition and processing device; and
    at least one phonocardiogram (PCG) sensor coupled to the signal acquisition and processing device, wherein the signal acquisition and processing device obtains a first set of waveforms from the phonocardiogram sensor, obtains a second set of waveforms from the blood-pressure waveform sensor, performs a signal processing or conditioning operation using the first and second sets of waveforms, determines a time delay between a dicrotic notch signal detected from the second set of waveforms and an S2 signal detected from the first set of waveforms, and determines a corrected blood pres sure pulse transit time value by adding S2D, representing a time delay between a patient's heart valve closure time and an arrival time of the S2 signal at the first distal location, to the time delay between a dicrotic notch signal and an S2 signal.

16. The system according to claim 15, wherein the signal acquisition and processing device includes a display device.

17. The system according to claim 15, wherein the blood pressure waveform measuring device includes a blood pressure cuff device.

18. The system according to claim 15, wherein the blood pressure waveform measuring device includes an arterial tonometer.

* * * * *